United States Patent
Jolly et al.

(10) Patent No.: US 8,750,988 B2
(45) Date of Patent: Jun. 10, 2014

(54) HYDROGEL-FILLED DRUG DELIVERY RESERVOIRS

(75) Inventors: Claude Jolly, Innsbruck (AT); Roland Hessler, Innsbruck (AT); Anandhan Dhanasingh, Herzogenrath (DE); Jürgen Groll, Niederstotzingen (DE)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 672 days.

(21) Appl. No.: 12/614,959

(22) Filed: Nov. 9, 2009

(65) Prior Publication Data

US 2010/0121422 A1    May 13, 2010

Related U.S. Application Data

(60) Provisional application No. 61/112,818, filed on Nov. 10, 2008, provisional application No. 61/243,209, filed on Sep. 17, 2009.

(51) Int. Cl.
*A61N 1/18* (2006.01)
*A61N 1/05* (2006.01)
*A61N 1/375* (2006.01)

(52) U.S. Cl.
CPC . *A61N 1/05* (2013.01); *A61N 1/375* (2013.01); *A61N 1/0568* (2013.01)
USPC ............ 607/3; 604/28; 604/891.1; 604/96.01

(58) Field of Classification Search
USPC .......................................... 607/3; 604/891.1
See application file for complete search history.

(56) References Cited

U.S. PATENT DOCUMENTS

| | | | |
|---|---|---|---|
| 4,207,554 A | 6/1980 | Resnick et al. | 382/133 |
| 4,400,590 A | 8/1983 | Michelson | 607/57 |
| 4,419,995 A | 12/1983 | Hochmair et al. | 607/57 |
| 4,573,994 A | 3/1986 | Fischell et al. | 604/891.1 |
| 4,588,394 A | 5/1986 | Schulte et al. | 604/9 |
| 5,087,243 A | 2/1992 | Avitall | 604/20 |
| 5,119,832 A | 6/1992 | Xavier | 128/786 |
| 5,215,085 A | 6/1993 | von Wallenberg-Pachaly | 607/57 |
| 5,458,631 A | 10/1995 | Xavier | 607/117 |
| 5,476,446 A | 12/1995 | Arenburg | 604/21 |
| 5,509,888 A | 4/1996 | Miller | 600/29 |
| 5,674,192 A * | 10/1997 | Sahatjian et al. | 604/28 |

(Continued)

FOREIGN PATENT DOCUMENTS

| | | | | |
|---|---|---|---|---|
| EP | 2047884 A1 | 4/2009 | | A61N 1/05 |
| WO | WO 99/00067 | 1/1999 | | A61B 19/00 |
| WO | WO 02/102278 A2 | 12/2002 | | |

*Primary Examiner* — Carl H Layno
*Assistant Examiner* — Jon Eric C Morales
(74) *Attorney, Agent, or Firm* — Sunstein Kann Murphy & Timbers LLP (57) ABSTRACT

A cochlear implant electrode includes an implantable electrode carrier having an outer surface with electrode contacts for electrically stimulating nerve tissue of the inner ear of a patient. A drug lumen is within the electrode carrier and adapted to receive a therapeutic fluid. The drug lumen contains delivery openings to the outer surface of the electrode carrier and a hydrogel matrix disposed between the drug lumen and the one or more delivery openings and adapted to swell in volume when exposed to the therapeutic fluid. The hydrogel matrix is adapted to control diffusion of the therapeutic fluid from the drug lumen through the delivery openings to the outer surface of the electrode carrier.

9 Claims, 10 Drawing Sheets

(56) References Cited

U.S. PATENT DOCUMENTS

| | | | |
|---|---|---|---|
| 5,676,655 A | 10/1997 | Howard et al. | 607/116 |
| 5,697,951 A | 12/1997 | Harpstead et al. | 607/3 |
| 5,713,847 A | 2/1998 | Howard et al. | 604/21 |
| 5,853,394 A | 12/1998 | Tolkoff et al. | 604/288.01 |
| 5,876,443 A | 3/1999 | Hochmair et al. | 623/10 |
| 5,891,183 A | 4/1999 | Zierhofer | 607/57 |
| 5,922,017 A | 7/1999 | Bredberg et al. | 607/137 |
| 5,928,229 A | 7/1999 | Gough et al. | 606/41 |
| 5,983,139 A | 11/1999 | Zierhofer | 607/56 |
| 5,997,524 A | 12/1999 | Burbank et al. | 604/506 |
| 5,999,859 A | 12/1999 | Jolly | 607/137 |
| D419,677 S | 1/2000 | McKimm | D24/175 |
| 6,119,044 A | 9/2000 | Kuzma | 607/137 |
| 6,129,685 A | 10/2000 | Howard, III | 600/585 |
| 6,156,728 A | 12/2000 | Gao | 514/12 |
| 6,157,861 A | 12/2000 | Faltys et al. | 607/57 |
| 6,176,879 B1 | 1/2001 | Reischi et al. | 623/11.11 |
| 6,195,586 B1 | 2/2001 | Kuzma | 607/137 |
| 6,231,604 B1 | 5/2001 | Von Ilberg | 623/10 |
| 6,259,951 B1 | 7/2001 | Kuzma et al. | 607/57 |
| 6,263,225 B1 | 7/2001 | Howard, III | 600/378 |
| 6,266,568 B1 | 7/2001 | Mann et al. | 607/137 |
| 6,309,410 B1 | 10/2001 | Kuzma et al. | 607/137 |
| 6,348,070 B1 | 2/2002 | Teissl et al. | 623/11.11 |
| 6,361,494 B1 | 3/2002 | Lindenthaler | 600/373 |
| 6,377,849 B1 | 4/2002 | Lenarz et al. | 604/21 |
| 6,397,110 B1 | 5/2002 | Kuzma | 607/137 |
| 6,440,102 B1 | 8/2002 | Arenberg et al. | 604/96.01 |
| 6,535,153 B1 | 3/2003 | Zierhofer | 341/143 |
| 6,556,870 B2 | 4/2003 | Zierhofer et al. | 607/57 |
| 6,594,525 B1 | 7/2003 | Zierhofer | 607/57 |
| 6,600,955 B1 | 7/2003 | Zierhofer | 607/57 |
| 6,628,991 B2 | 9/2003 | Kuzma et al. | 607/137 |
| 6,661,363 B2 | 12/2003 | Zierhofer | 341/143 |
| 6,727,833 B2 | 4/2004 | Zierhofer | |
| 6,838,963 B2 | 1/2005 | Zimmerling et al. | 335/205 |
| 6,862,805 B1 | 3/2005 | Kuzma et al. | 29/858 |
| 6,968,238 B1 | 11/2005 | Kuzma | 607/137 |
| 7,044,942 B2 | 5/2006 | Jolly et al. | 607/891.1 |
| 7,050,858 B1 | 5/2006 | Kuzma et al. | 607/137 |
| 7,319,906 B2 | 1/2008 | Kuzma et al. | 607/137 |
| 2001/0031996 A1 | 10/2001 | Leysieffer | 607/57 |
| 2001/0049466 A1 | 12/2001 | Leysieffer et al. | 600/25 |
| 2002/0019669 A1 | 2/2002 | Berrang et al. | 623/10 |
| 2002/0082554 A1 | 6/2002 | Lenarz et al. | 604/104 |
| 2003/0097121 A1 | 5/2003 | Jolly et al. | 604/891.1 |
| 2004/0039245 A1 | 2/2004 | Jaeger et al. | 600/25 |
| 2004/0127968 A1 | 7/2004 | Kuzma et al. | 607/137 |
| 2004/0133250 A1 | 7/2004 | Ball et al. | 607/57 |
| 2004/0172005 A1 | 9/2004 | Arenberg et al. | 604/514 |
| 2004/0196169 A1 | 10/2004 | Zierhofer | 341/143 |
| 2004/0220651 A1 | 11/2004 | Kuzma et al. | 607/137 |
| 2005/0062567 A1 | 3/2005 | Zimmerling et al. | 335/150 |
| 2006/0009806 A1* | 1/2006 | Heruth et al. | 607/3 |
| 2006/0264897 A1 | 11/2006 | Lobl et al. | 604/506 |
| 2007/0088335 A1* | 4/2007 | Jolly | 604/891.1 |
| 2007/0088355 A9 | 4/2007 | Auth et al. | 606/49 |
| 2007/0106360 A1 | 5/2007 | Gibson et al. | 607/137 |
| 2007/0255236 A1 | 11/2007 | Christenson et al. | 604/288.01 |
| 2007/0255237 A1 | 11/2007 | Lobl et al. | 604/288.01 |

* cited by examiner

HYDROGEL-FILLED DRUG DELIVERY RESERVOIRS

This application claims priority from U.S. Provisional Patent 61/112,818, filed Nov. 10, 2008, and U.S. Provisional Patent 61/243,209, filed Sep. 17, 2009, which are incorporated herein by reference.

FIELD OF THE INVENTION

The present invention relates to medical implants, and more specifically to implantable drug delivery systems for the inner ear.

BACKGROUND ART

There is increased interest in implantable drug delivery systems to deliver therapeutic fluids to targeted internal tissues such as the inner ear. Drug eluting electrode leads with cortico steroids have been used successfully in the past with cardiac pacemaker electrodes to reduce the contact impedance. In addition, silicone elastomer loaded with a pharmacological agent has been used as an eluting structure in several applications such as birth control, vascular injury treatment, and stents. There also have been attempts to deliver medicine to the inner ear, for example to promote healing after implantation of cochlear implant electrode.

But materials that release a therapeutic substance do not necessarily have a desirable linear release rate and/or may not be refillable (e.g. NuvaRing® birth control device). Large complex implantable drug delivery pumps (e.g. from tricumed Medizintechnik GmbH) are known for implantation in body regions such as the abdomen for delivering significant amounts of therapeutic fluids into the circulatory system. However this technology is designed to deliver relatively large amounts of drugs in body locations which are less fragile and which allow greater implant dimensions than the inner ear.

In US 2009/062896 A1, the inventor describes a nonlinear release profile as illustrated in his FIG. 13. His FIG. 16 shows that this release profile is achieved by loading different forms of the drug dexamethasone, such as dexamethasone salt and dexamethasone base, into a storage lumen.

WO0241666 describes an electrode carrier having a drug impregnated bioresorbable gel that when implanted in a patient releases the drug over time. During manufacture, the electrode must be soaked in the liquid drug for long enough to absorb the chemical. Then the liquid must be dried out for packaging and shipment, and when the electrode is implanted, it absorbs fluid and refoms the gel which then releases the drug over time.

SUMMARY OF THE INVENTION

Embodiments of the present invention are directed to a cochlear implant electrode that includes an implantable electrode carrier having an outer surface with electrode contacts for electrically stimulating nerve tissue of the inner ear of a patient. A drug lumen is within the electrode carrier and adapted to receive a therapeutic fluid. The drug lumen contains delivery openings to the outer surface of the electrode carrier and a hydrogel matrix disposed between the drug lumen and the one or more delivery openings and adapted to swell in volume when exposed to the therapeutic fluid. The hydrogel matrix is adapted to control diffusion of the therapeutic fluid from the drug lumen through the delivery openings to the outer surface of the electrode carrier.

The drug lumen may be adapted to contain a treatment period amount of therapeutic fluid for an extended treatment period. The hydrogel matrix may be based on a three-dimensional network of cross-linked hydrophilic polymer chains, for example, made of hyaluronic acid. The hydrogel matrix may have a mesh size small enough to resist entry of bacteria. The hydrogel matrix may fill some or all of the volume of the lumen. The hydrogel matrix may have an adjustable pore size which controls diffusion rate of the therapeutic fluid.

The therapeutic fluid may include dexamethasone, for example, the electrode array may be adapted to release between 5 µg and 600 µg of dexamethasone during an initial 24 hour period of use. There may be a refilling arrangement for refilling the drug lumen in an implanted electrode with additional therapeutic fluid.

BRIEF DESCRIPTION OF THE DRAWINGS

FIG. 11A-B shows an embodiment of an electrode having an inner drug lumen with a hydrogel matrix that fills some or all of the lumen.

FIG. 13A-B shows drug diffusion characteristics of drug lumens with and without a hydrogel matrix.

FIG. 16A-C shows how an embodiment of a drug lumen and hydrogel matrix is filled with a therapeutic fluid.

DETAILED DESCRIPTION OF SPECIFIC EMBODIMENTS

Various embodiments of the present invention are directed to implantable drug delivery apparatuses and methods. Embodiments include a fillable and refillable implantable drug delivery system which does not increase its internal pressure while refilling. And electrical and/or magnetic pulses can be used to displace molecules within the therapeutic fluid within the apparatus. Such embodiments and techniques are useful for delivering a solution of a therapeutic fluid into target tissue such as a body cavity like the cochlea. Embodiments also include one or more subcutaneous drug delivery reservoirs that are transcutaneously refillable without increasing pressure. Embodiments also maintain homogeneity of a therapeutic fluid within a drug delivery reservoir as the drug diffuses to the outside of the reservoir. Embodiments of the invention also include an implantable electrode carrier having a drug lumen that contains a hydrogel matrix which allows diffusion over time of a therapeutic fluid from the lumen into tissue adjacent to the electrode carrier.

Figure 1:
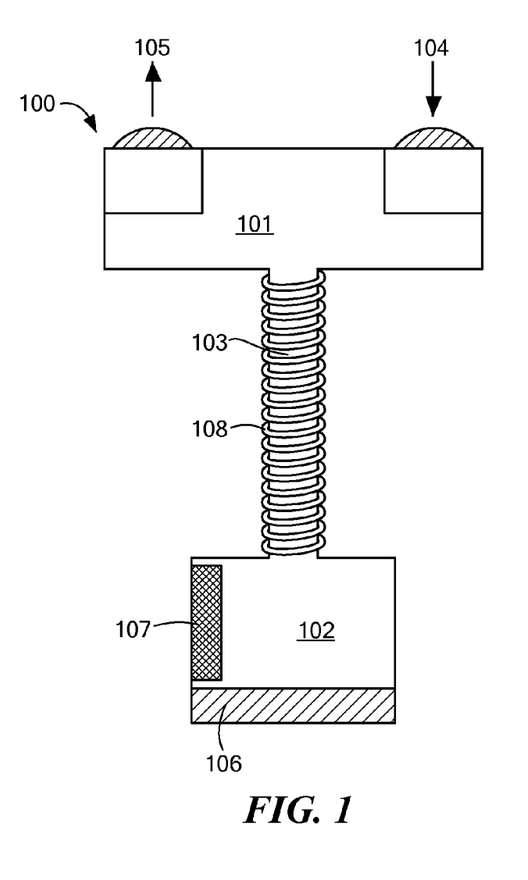
FIG. 1 shows an embodiment of an implantable drug delivery system.

FIG. 1 shows an embodiment of an implantable drug delivery system 100 that includes a subcutaneous primary reservoir 101 that holds a primary volume of a therapeutic fluid. The primary reservoir 101 includes an input port septum 104 for receiving the therapeutic fluid and a corresponding an output port septum 105 for removing fluid. A diffusion channel 103 provides a fluid communication path from the primary reservoir 101 to a secondary reservoir 102 that holds a secondary volume of the therapeutic fluid. The secondary reservoir 102 includes a drug permeable surface 107 such as a drug permeable membrane, slits or holes for diffusion of the therapeutic fluid into nearby tissue, and a priming septum 106 for fluid exchange within the secondary reservoir 102. It may be useful in such an arrangement to mix the therapeutic fluid with an osmotic agent such as a saline solution for promoting and accelerating diffusion of the therapeutic fluid out of the secondary reservoir 102. The embodiment shown in FIG. 1 also includes a channel coil 108 that surrounds the diffusion channel 103 for inducing ionic displacement of fluid within the diffusion channel from one reservoir to the other.

The system may be filled with therapeutic fluid before implantation by inserting a needle of a delivery syringe containing the therapeutic fluid into the input port septum 104. A needle of a receiver syringe is inserted into the priming septum 106 and the therapeutic fluid is injected from the delivery syringe into the primary reservoir 101 while the receiver syringe withdraws fluid from the secondary reservoir 102, thereby priming the reservoirs with the therapeutic fluid fluid. After priming the system, the needles are removed from the septums and the drug delivery system is ready to be subcutaneously implanted in a selected position in a patient, for example, adjacent to the skull of the patient for use with a cochlear implant system.

The implantable drug delivery system 100 allows refilling of the reservoirs 101 and 102, either with the same therapeutic fluid or with a new therapeutic fluid with a different molecular content. The refilling process does not raise pressure either within the internal volume of the drug delivery system 100 or in the surrounding tissue and fluid region outside the secondary reservoir 102. No special bacterial filter is needed because molecular diffusion preferentially occurs through the ion permeable membrane drug delivery surface 107, or through punctures in the drug delivery surface 107 that are smaller than bacteria size.

Figure 2:
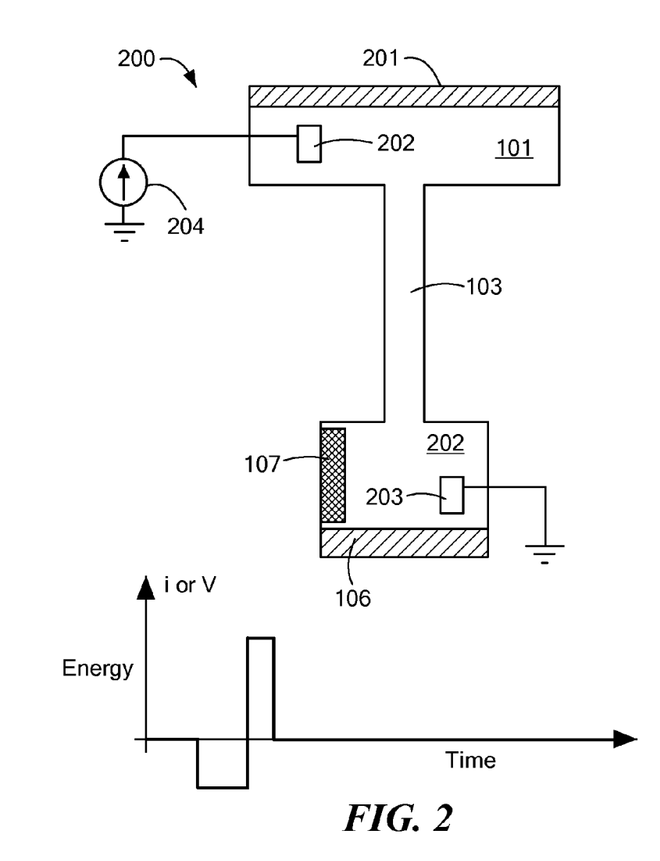
FIG. 2 shows another embodiment of an implantable drug delivery system using a charge drive arrangement.

FIG. 2 shows another similar embodiment of an implantable drug delivery system 200 which has just a single primary septum 201 on top of the primary reservoir 101. And instead of a channel coil arrangement, this embodiment uses a charge driver arrangement to for displacing the therapeutic fluid within the apparatus by driving electrically charged molecular substances within the therapeutic fluid. Specifically, a pulse generator 204 (e.g., from an implantable stimulator) generates a drive signal to an active electrode 202 in the primary reservoir 101. A ground electrode 203 in the secondary reservoir 102 completes the current path. A drive signal based on charge balanced asymmetric pulses such as the example shown in the bottom of FIG. 2 then can drive electrically charged molecular substances within the therapeutic fluid, for example, to displace the therapeutic fluid from the primary reservoir 101 to the secondary reservoir 102 over time to replenish the secondary reservoir.

Instead of placing the ground electrode 203 inside the secondary reservoir 102, in some embodiments it may be external to the secondary reservoir 102. Such an arrangement allows a drive signal based on charge balanced asymmetric pulses to displace the therapeutic fluid from the primary reservoir 101, through the secondary reservoir 102, and by active diffusion through the drug permeable surface 107 into the nearby tissue, e.g., into the surrounding cochlear fluid or extra-cellular fluid. Such a charge driver arrangement may be especially effective if there are small ionic channels between the polymer matrix of the drug permeable surface 107 and the surrounding tissue. These can be created by punctures made with a small needle, laser ablation of holes, use of an ion permeable membrane, and/or one or more slits from scalpel, any of which may provide an improved passage for the flow of complex charged molecules in the therapeutic fluid to flow from inside the secondary reservoir 102 out into the surrounding fluids and tissues.

Using a balanced charge drive signal may help avoid undesirable corrosion of the electrodes 202 and 203. The pulse generator 204 advantageously may be located within the housing of a cochlear implant stimulator, which typically are designed to deliver charge balanced symmetric or asymmetric pulses. Alternatively the drive signal may be based on use of tri-phasic pulses to provoke a net charge displacement in one direction of the electrodes. The associated insulated wiring for such embodiments both to and from the pulse generator 204 and between the electrodes 202 and 203 may run within the interior volume of the reservoirs, or within or along the walls and surfaces of the apparatus structures.

Figure 3:
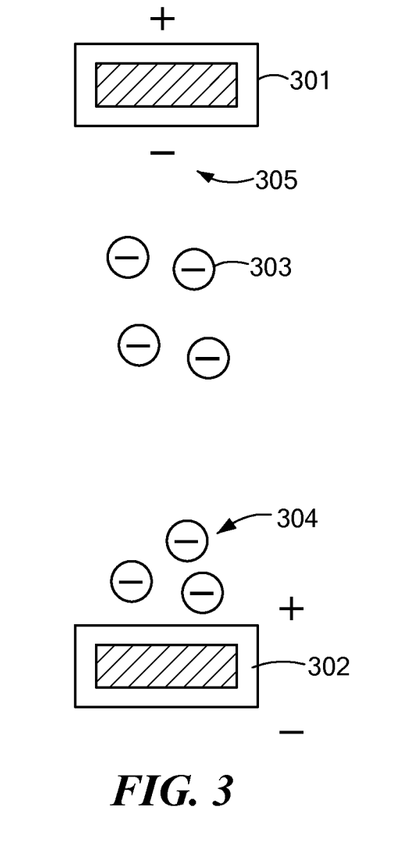
FIG. 3 shows principles of a magnetic drive arrangement as used by another embodiment of the present invention.

Rather than a charge drive arrangement as depicted in FIG. 2, some embodiments may use a magnetic drive arrangement based on the principles shown in FIG. 3 for displacing the therapeutic fluid within the apparatus by driving magnetic molecular substances within the therapeutic fluid. Instead of electrodes 203 and 204, a magnetic driver arrangement uses a repeller magnet 301 and an attractor magnet 302 that set up a magnetic field between them that displaces the therapeutic fluid within the apparatus by driving magnetic molecular substances 303 within the therapeutic fluid. In the example shown in FIG. 3, this drives the magnetic molecules away from the repeller magnet 301 to create a region of lower molecular concentration 305 in the vicinity, while a higher molecular concentration 304 region develops near to the attractor magnet 302 located, for example, outside the secondary reservoir to exert a magnetic attractive force on magnetic molecular substances within the therapeutic fluid and pull them through the drug permeable surface into the nearby tissue. Alternatively, the attractor magnet 302 may be located within the secondary reservoir to displace the therapeutic fluid from the primary reservoir to the secondary reservoir over time to replenish the secondary reservoir. The magnets 301 and/or 302 may usefully be covered by a protective encapsulation layer.

Figure 4:
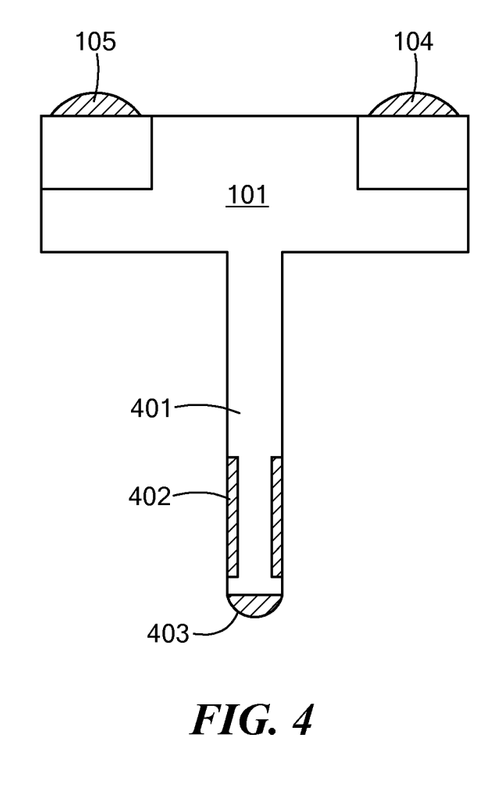
FIG. 4 shows an embodiment having a volume of therapeutic fluid in a delivery catheter.

FIG. 4 shows another embodiment of an implantable drug delivery apparatus in which the arrangement of the primary reservoir 101 and its input septum 104 and output septum 105 are as in FIG. 1, but the secondary reservoir 401 is elongated to form a delivery catheter that encloses the secondary volume. Thus, the proximal end of delivery catheter secondary reservoir 401 is in fluid communication with the input septum 104 while the distal end includes an output septum 403 for removing fluid from the secondary reservoir 401 when filling or refilling the system. A drug permeable surface 402 such as an ion permeable diffusion membrane diffuses the therapeutic fluid into the surrounding tissues and fluids.

Figure 5:
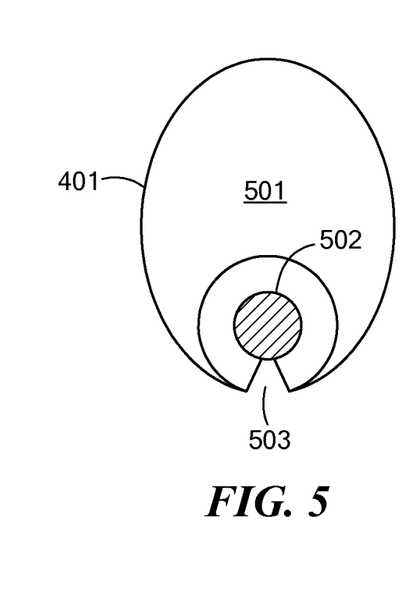
FIG. 5 shows an embodiment having a semi-permeable filter in the form of a drug delivery rod.

In some embodiments, the interior of the secondary reservoir 401 may include a semi-permeable filter such as the drug delivery rod 502 shown in FIG. 5 for mechanically filtering fluid flow through the catheter. In the example shown, the drug delivery rod 502 may be in the specific form of a drug eluting gel or drug eluting polymer such as a drug eluting silicone rod. Such a drug delivery rod 502 is then embedded or incorporated into the main superstructure of the secondary reservoir 401, which may be, for example, a silicone matrix 501. The silicone matrix 501 may include a slit opening 503 that allows hydration of the drug eluting material by the surrounding fluid. In some embodiments, the elongated form of the secondary reservoir 401 may be pre-shaped to have a bend in it to accommodate placement around internal body structures. Or the secondary reservoir 401 may be flexible to be bendable around such internal body structures.

Figure 6:
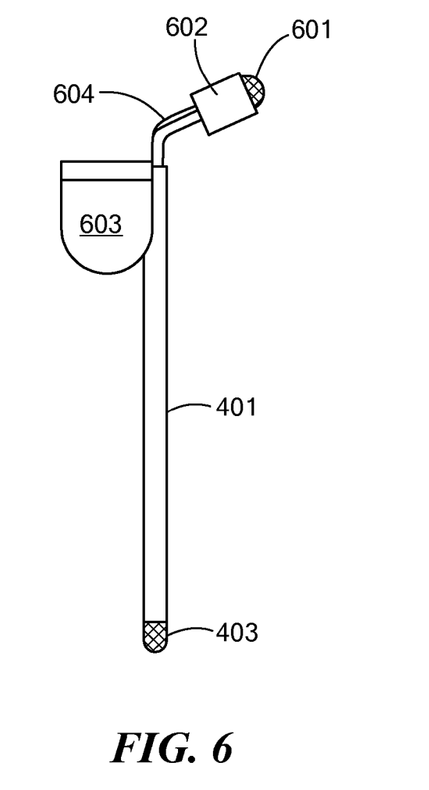
FIG. 6 shows an embodiment in which an implantable delivery catheter is connected to the body of an implant housing.

FIG. 6 shows another embodiment in which an implantable delivery catheter 401 is connected to the body of an implant housing 603, such as a cochlear implant stimulator housing. In such an embodiment, the delivery catheter 401 may be an internal volume within a stimulator electrode array which is implanted, for example, in the cochlea of a hearing impaired patient. The electrode array in such an embodiment includes a drug permeable surface as described above (e.g., an ion or molecule permeable membrane and/or an arrangement of multiple diffusion slits or holes) through which the therapeutic fluid diffuses into the surrounding tissue or fluid. In the embodiment shown, the therapeutic fluid is delivered to the delivery catheter 401 via an arrangement of an input septum 601 over an input port 602, through an input channel 604 and the implant housing 603. In another embodiment, there may be simply an input septum 601 without a discernable defined input port 602 as such. In either configuration, priming septum 106 may be used before implantation to withdraw existing fluid within the delivery catheter 401 to initially fill the system. After implantation, additional therapeutic fluid can be periodically added transcutaneously through the input septum 601, which located is just under the skin of the patient.

Figure 7:
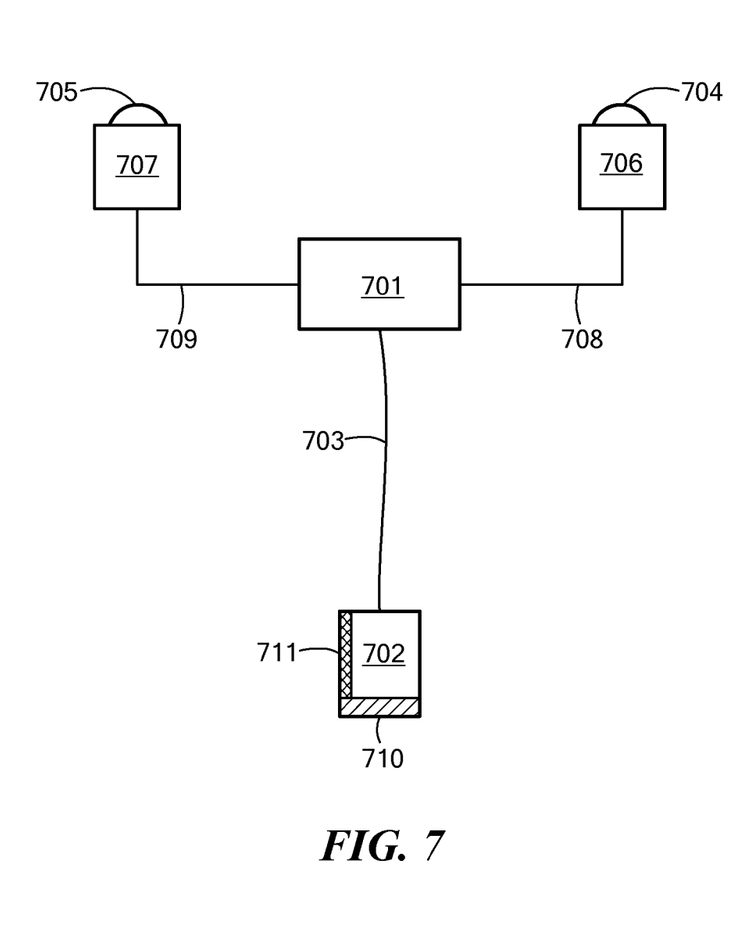
FIG. 7 shows another embodiment having a primary reservoir and a secondary reservoir connected by a diffusion channel.

FIG. 7 shows another embodiment having a primary reservoir 701 and a secondary reservoir 702 connected by a diffusion channel 703. The secondary reservoir 702 includes a priming septum 710 and a drug delivery surface 711 as described above with regards to other embodiments. In addition, an input channel 708 provides fluid communication between the primary reservoir 701 and an input port 706 having an input septum 704. Similarly, an output channel 709 also provides fluid communication between the primary reservoir 701 and an output port 707 having an output septum 705.

Initial filling of the system may occur before implantation using the input septum 704 and priming septum 710. After implantation, the system can be filled/replenished using a delivery syringe containing the therapeutic fluid to refill the primary reservoir 701 transcutaneously through the skin of a patient into the input septum 704, while a receiver syringe under negative pressure (i.e., withdrawing the plunger) permits air or old fluid to be withdrawn transcutaneously through the output septum 705 and the skin into the receiver syringe, thereby refilling/replenishing the primary reservoir 701. After the therapeutic fluid has been introduced into the primary reservoir 701, both the delivery syringe needle and the receiver needle are removed.

Figure 8A:
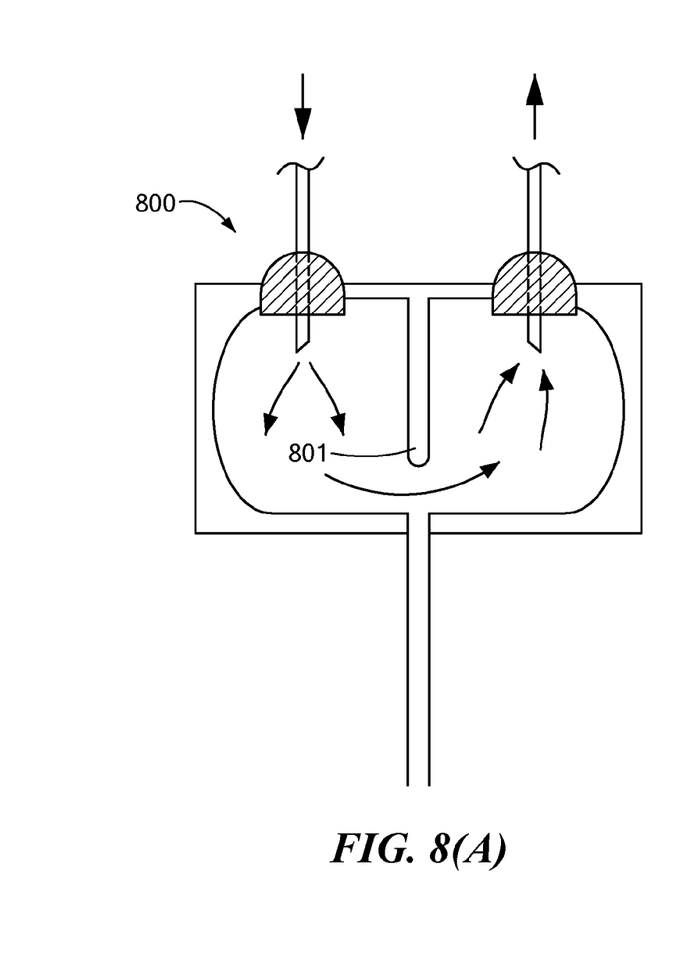
FIG. 8 shows an embodiment having one or more internal control surfaces to form a control labyrinth that promotes controlled flow of fluid.
Figure 8B:
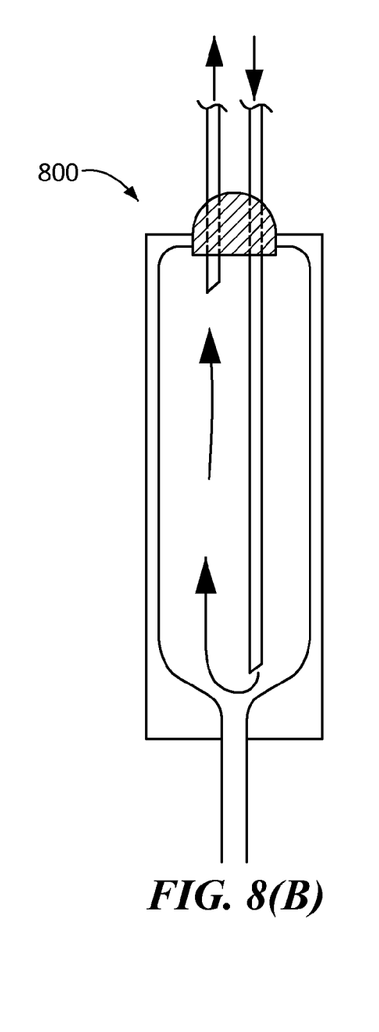

Embodiments may also include an internal flow control arrangement for correctly and reliably directing fluid flow within the primary reservoir, for example to maintain a desired concentration of therapeutic fluid within the fluid in the reservoir. For example, FIG. 8 shows a primary reservoir 800 having one or more internal control surfaces 801 to form a control labyrinth that promotes controlled flow of fluid within the primary reservoir 800. FIG. 8A shows use of a single control surface 801, in other embodiments, there may be multiple such control surfaces arranged to form a more complicated control labyrinth. For example, a capillary tube arrangement such as the one shown at the bottom of FIG. 9 may be used as a control labyrinth within the primary reservoir 800.

Figure 9:
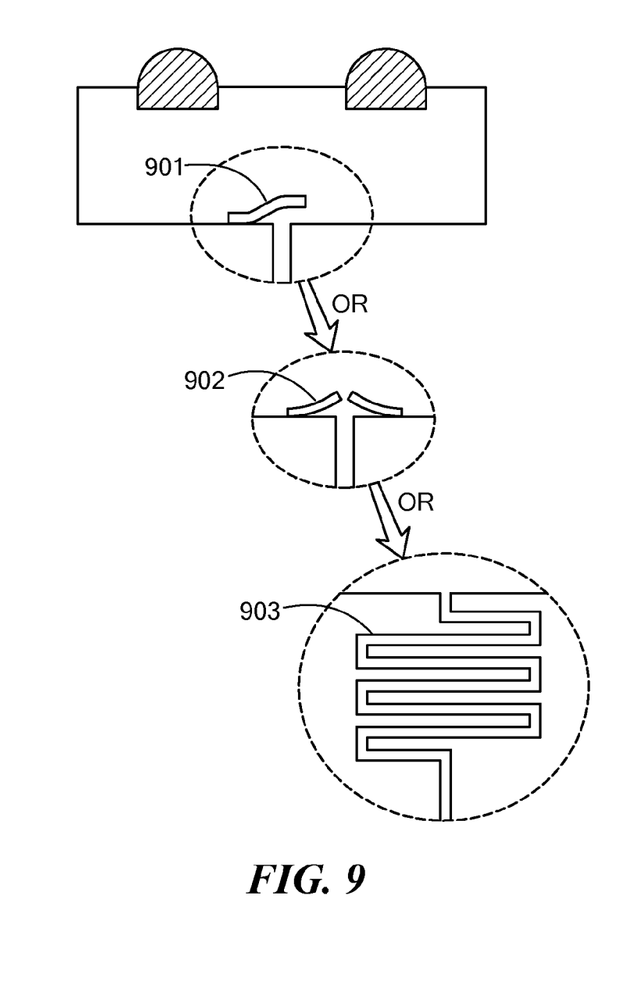
FIG. 9 shows an embodiment having a pressure control element between the primary reservoir and the secondary reservoir for preventing pressure transients.

Embodiments may also include a pressure control element between the primary reservoir and the secondary reservoir for preventing pressure transients between the primary reservoir and the secondary reservoir. Limiting pressure transients between the primary reservoir and the secondary reservoir during fluid filling operations also serves to prevent pressure transients in the surrounding tissue and fluid region outside the secondary reservoir. For example, such a pressure control element may be in the specific form of a check valve arrangement at the opening to the diffusion channel such as single flap check valve 901 or double flap check valve 902. If pressure increases in the primary reservoir during fluid filling, the check valve 901 or 902 closes to prevent a pressure transient in the secondary reservoir. Alternatively, a capillary tube arrangement 903 at the beginning of the diffusion channel may serve the same purpose by allowing diffusion but providing significant resistance to any pressure driven fluid flow.

Figure 10:
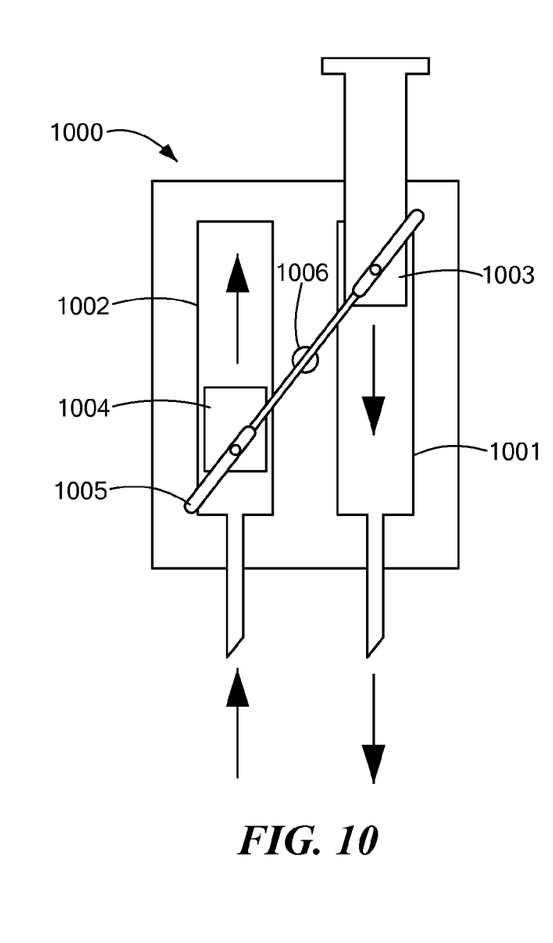
FIG. 10 shows a device having a delivery syringe and a receiver syringe in accordance with an embodiment of the present invention.

To maintain constant pressure in the reservoirs, the fluid flow into and out of the system needs to be coordinated in volume and flow rate. This can be achieved with a device or arrangement which takes in and out of the reservoir, the same amount of fluid, at the same time and the same flow rate. FIG. 10 shows one example of such a fluid replacement device 1000 which contains in a single housing both a delivery syringe 1001 having a delivery piston 1003 and a receiver syringe 1002 having a receiver piston 1004. Connected to each piston is a piston coupling rod 1005 which rotates about a coupling axis 1006 so that when the delivery piston is pushed into the delivery syringe 1001, the coupling rod 1005 rotates to push out the receiver piston 1004 the same amount.

Figure 11A:
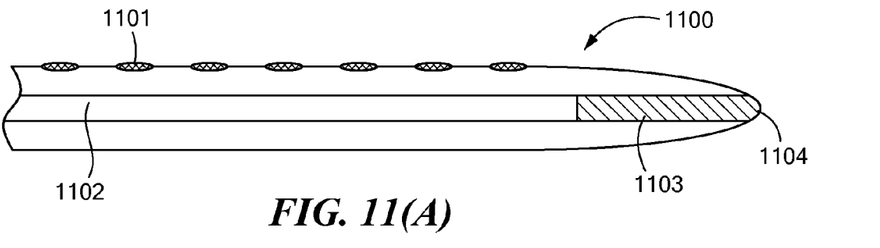

Embodiments of the present invention also are directed to a cochlear implant electrode as shown in FIG. 11A-B that includes an implantable electrode carrier 1100 having an outer surface with electrode contacts 1101 for electrically stimulating nerve tissue of the inner ear of a patient. A drug lumen 1102 is within the electrode carrier 1100 and adapted to receive a therapeutic fluid, for example, a treatment period amount of a therapeutic fluid such as dexamethasone. So the drug lumen 1102 may contain a treatment volume of dexamethasone to release between 5 μg and 600 μg of dexamethasone during an initial 24 hour period of use.

Figure 11B:
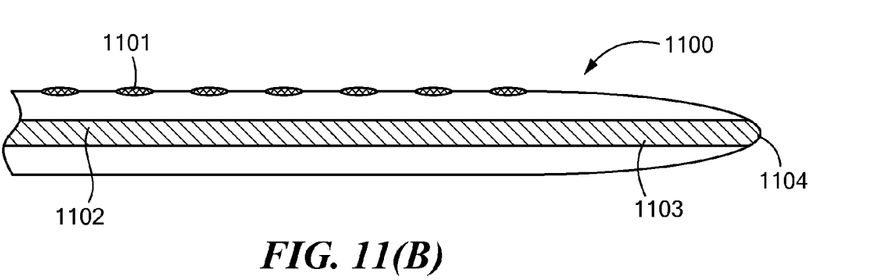

The drug lumen 1102 also contains one or more delivery openings 1104 to the outer surface of the electrode carrier 1100. A hydrogel matrix 1103 is disposed between the drug lumen 1102 and the one or more delivery openings 1104 and adapted to swell in volume when exposed to the therapeutic fluid. The hydrogel matrix 1103 is adapted to control the diffusion of the therapeutic fluid from the drug lumen 1102 through the one or more delivery openings 1104 to the outer surface of the electrode carrier 1100. In the embodiment shown in FIG. 11A, the hydrogel matrix 1103 fills a portion of the drug lumen 1102 nearest the opening. FIG. 11B shows a similar embodiment where the hydrogel matrix 1103 fills the entire volume of the drug lumen 1102.

Figure 12:
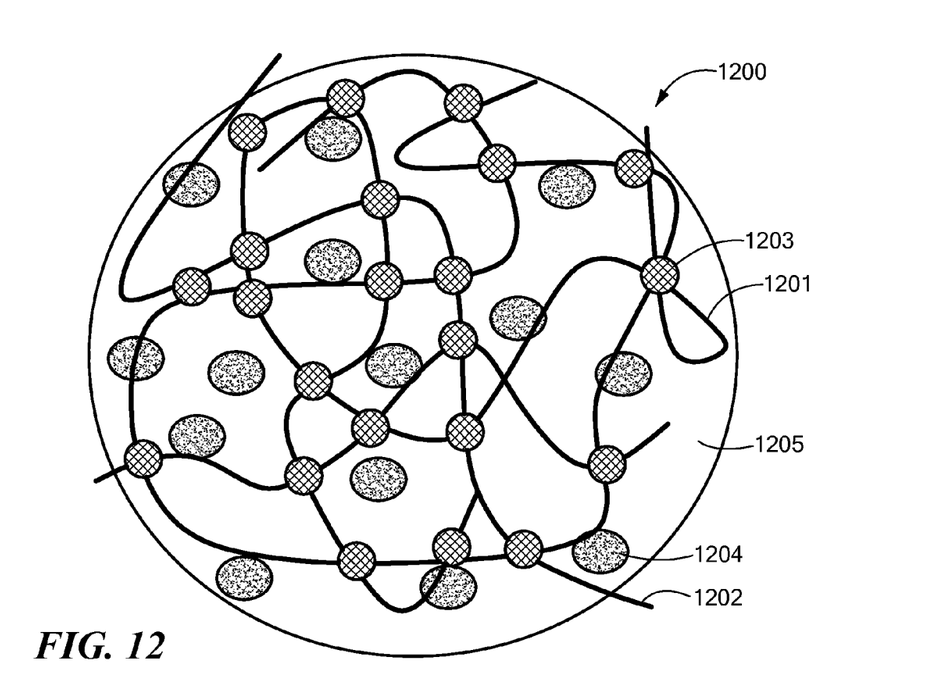
FIG. 12 shows a hydrophilic polymer network used for a hydrogel matrix according to one embodiment.

The hydrogel matrix 1103 may be based on hyaluronic acid in a three-dimensional network. FIG. 12 shows a hydrophilic polymer network 1200 that forms multiple cross-linked hydrophilic polymer chains which include closed loops 1201 and dangling ends 1202. The polymer network 1200 also includes cross-linking points 1203 and polar groups 1204 that make the polymer hydrophilic. The hydrogel matrix 1103 acts as a host to the therapeutic fluid inside the drug lumen 1102. The hydrogel matrix 1103 allows the drug lumen 1102 to store the molecules of the therapeutic fluid both in a dry status (for example on the shelf) and in a wet status (for example when implanted). When the polymer network 1200 is immersed in water 1205 it increases in volume, and the therapeutic fluid can diffuse out from the drug lumen 1102 through the polymer network 1200 at a diffusion rate that is controlled by the pore size of the hydrogel matrix 1103 which preferably also is small enough to resist entry of bacteria.

In specific embodiments, the hydrogel matrix 1103 may be non-degradable, partially biodegradable, or fully biodegradable. It would be possible to arrange the hydrogel matrix 1103 in the drug lumen 1102 so that some sections of the lumen are filled with biodegradable hydrogel, while other sections have non-degradable hydrogel. The hydrogel matrix 1103 is vacuum- and temperature-resistant such that it is suitable for sterilization.

In an embodiment where the drug lumen 1102 is partially filled with a hydrogel matrix 1103 (e.g., FIG. 11B), the hydrogel matrix 1103 can act as a diffusion gate for the therapeutic fluid. A diffusion gate could also be one or more small delivery openings (for example punctures or slits) in the side wall of the drug lumen 1102. When the concentration of the therapeutic fluid is greater within the drug lumen 1102 than outside the electrode carrier 1100 so as to form a concentration gradient, then the therapeutic fluid will diffuse out of the drug lumen 1102 over time into target tissue adjacent to the electrode carrier 1100.

Figure 13A:
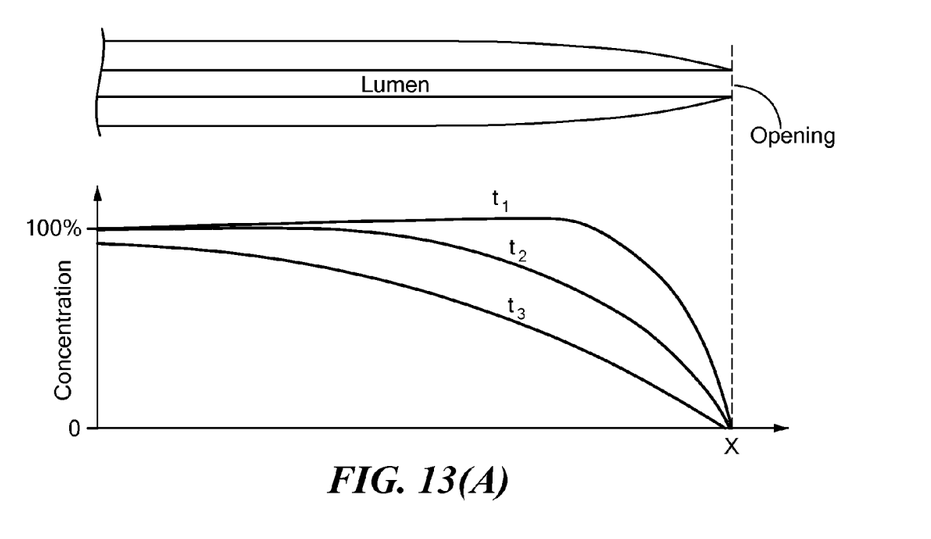
Figure 13B:
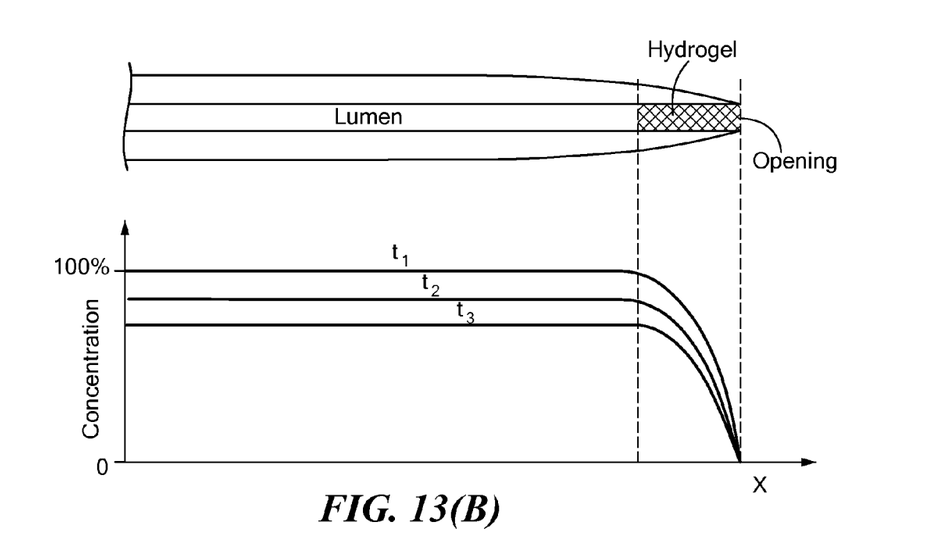
Figure 14:
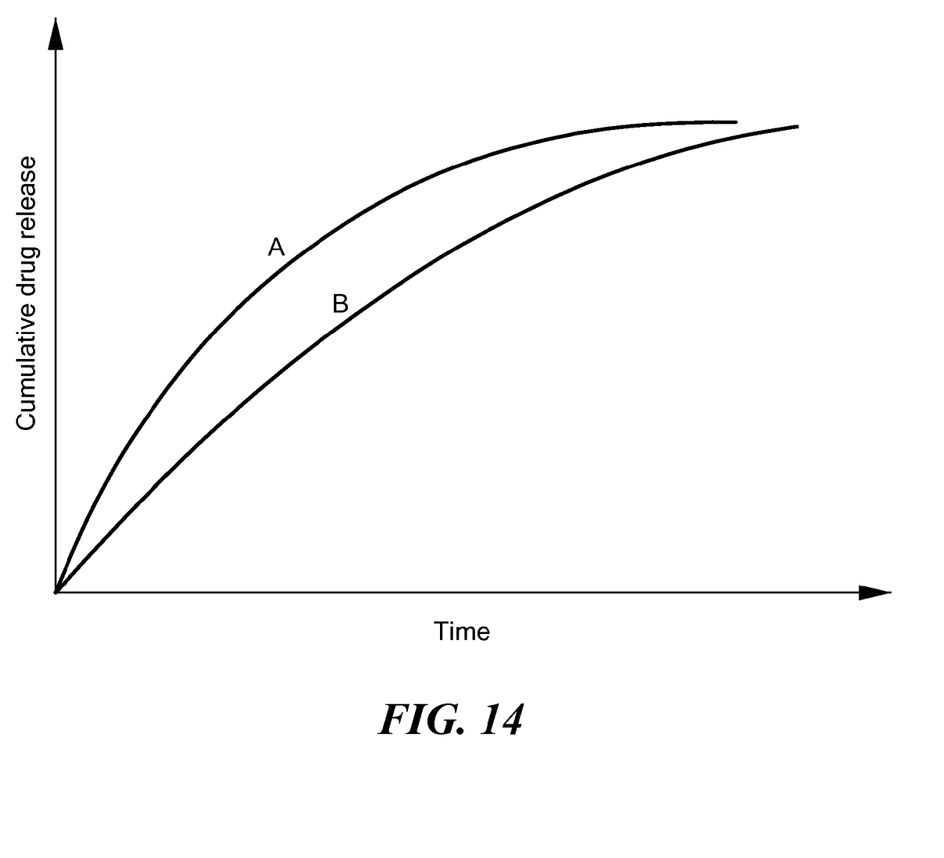
FIG. 14 shows drug release profile curves for drug lumens with and without a hydrogel matrix.

It is useful to compare the characteristics of an implantable electrode carrier 1100 containing a drug lumen 1102 both with and without a hydrogel matrix 1103. FIG. 13A shows the drug diffusion characteristics for a drug lumen 1102 without a hydrogel matrix 1103 at the one or more delivery openings 1104, where a flat concentration gradient develops while the therapeutic fluid diffuses out of the drug lumen 1102. Curve A in FIG. 14 shows the resulting non-linear drug release profile over time with large release rates in the beginning and lower release rates towards the end of the release time. FIG. 13B shows the drug diffusion characteristics for a drug lumen 1102 with a hydrogel matrix 1103 at the one or more delivery openings 1104 where the drug diffusion coefficient in the section without the hydrogel matrix 1103 is much higher than the drug diffusion coefficient in the section with the hydrogel matrix 1103. Thus, the diffusion rate through the hydrogel matrix 1103 is the time dependent factor rather than diffusion rate within the section of the drug lumen 1102 without the hydrogel matrix 1103. This allows enough time for the drug concentration within the drug lumen 1102 to even out, resulting in a steep concentration gradient in the section with the hydrogel matrix 1103 as seen in FIG. 13B. While the drug lumen 1102 releases the therapeutic fluid, the drug concentration gradient changes less in the section with the hydrogel matrix 1103 which leads to a more linear drug release profile as shown in Curve B of FIG. 14.

After mixing the hydrogel material from its constituent compounds, the hydrogel stays in liquid form for a period. The liquid hydrogel material can be easily positioned either partially or fully into the drug lumen 1102, for example, by injection. Polymerization of the hydrogel material then occurs within the drug lumen 1102 ending with the hydrogel matrix 1103 being solid and fixed within the drug lumen 1102. To mechanically fix the hydrogel matrix 1103 within the drug lumen 1102, the front end of the drug lumen 1102 can be closed and one or more delivery openings 1604 provided at the side of the lumen as shown in FIG. 16. This type of design prevents the hydrogel matrix 1103 from popping out of the drug lumen 1102 when fluid pressure is applied.

The hydrogel matrix 1103 also acts as a flow resistor and pressure resistance. In a refillable reservoir arrangement such as the one shown in FIG. 4, a primary reservoir is flushed using two fluid septums 104 and 105. Such a refilling procedure could cause pressure differentials that could be transferred to fragile pressure sensitive regions such as the inner ear. A hydrogel matrix 402 can be used to avoid such behavior. The hydrogel matrix 402 minimizes the flow of liquid out of the tip of the reservoir so that the therapeutic fluid is only released by diffusion through the hydrogel matrix 402 and is not actively driven by the refilling pressure.

Figure 15:
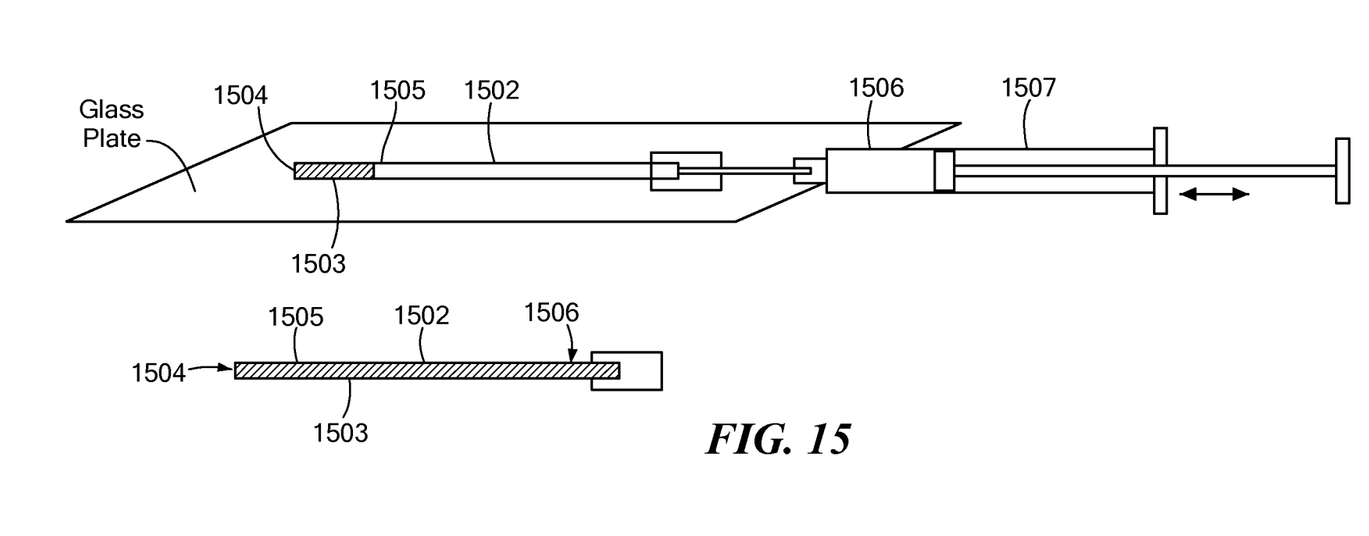
FIG. 15 shows an arrangement for loading therapeutic fluid into a drug lumen.

If an electrode has a drug lumen 1102 which uses a permeable membrane with its one or more delivery openings 1104, then it is not possible to fill the lumen because the air it contains cannot be released. But if there is a permanent outlet to release this air, then body fluids and/or bacteria may enter the drug lumen 1102. FIG. 15 shows an arrangement for loading therapeutic fluid 1506 into a drug lumen 1502 containing a hydrogel matrix 1503 and a pin hole 1505 near the delivery opening 1504 that allows air to be released from the drug lumen 1502 while filling it with the therapeutic fluid 1506 from a drug syringe 1507. After filling, the pin hole 1505 does not release any liquid from the drug lumen 1502. In some embodiments, the therapeutic fluid 1506 can be loaded into a drug lumen 1502 while the hydrogel material is dry. The therapeutic fluid 1506 can be injected through a septum or similar structure at the back end of the drug lumen 1502 while air is released through the pores of the dry hydrogel. Once the liquid of the therapeutic fluid 1506 begins to flow through the dry hydrogel material, it swells up into a hydrogel matrix 1503 and seals the one or more delivery openings 1504 at the front end of the drug lumen 1502. In some embodiments, the delivery openings 1504 may include a permeable membrane to further benefit this arrangement.

Figures 16A, 16B:
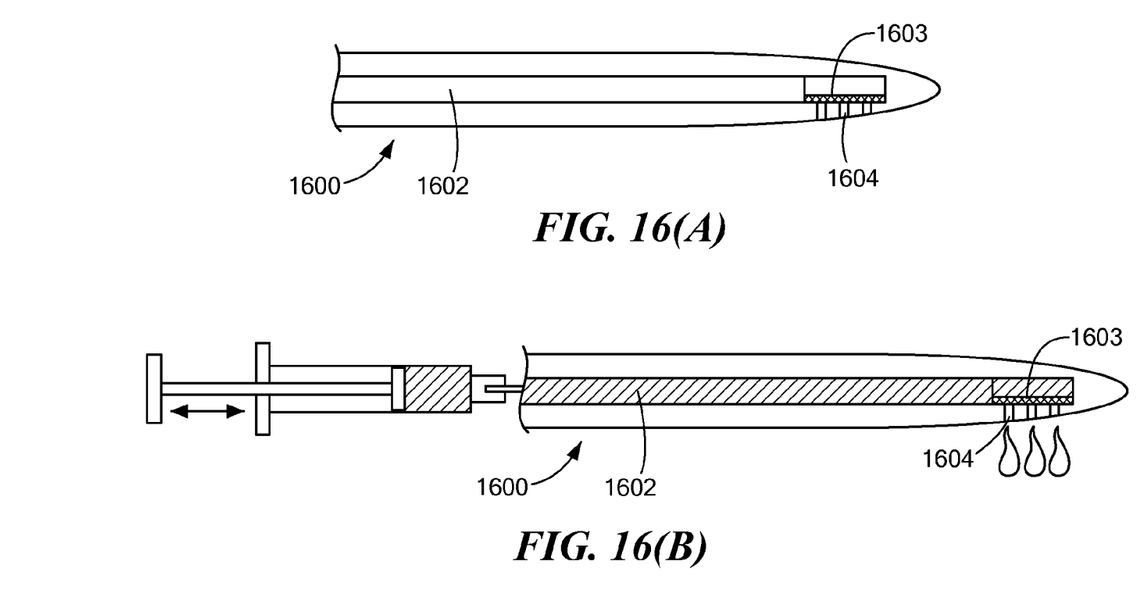
Figure 16C:
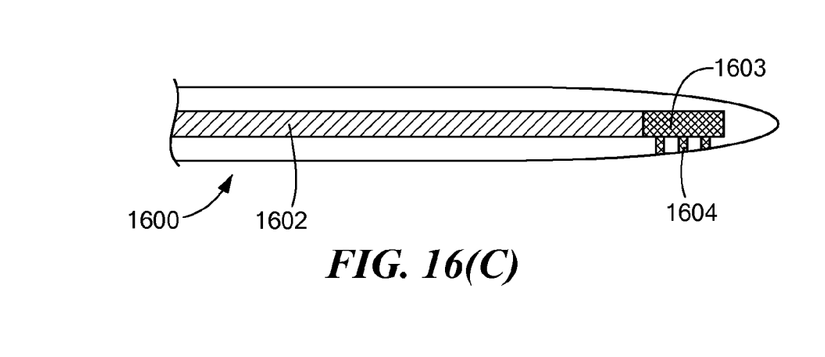

FIG. 16A shows an electrode carrier 1600 having an empty drug lumen 1602 which does not initially contain any therapeutic fluid, but which does contain the dry hydrogel material. This is a convenient shelf-stable form in which to transport and store the electrode carrier 1600 prior to implantation by a surgeon in a patient. The therapeutic fluid may be added at any convenient time after manufacturing, e.g., directly prior to implantation. Then during surgery the surgeon can decide what kind of medication he requires and then inject the therapeutic fluid with a syringe into the empty drug lumen 1602 as shown in FIG. 16B. During the drug injection, the air can be released from the drug lumen 1602 through the dry hydrogel material. The initial volume of the dry hydrogel material is just a fraction (e.g. up to 20%) of its final volume when wet into the swollen hydrogel matrix 1603. As the injected therapeutic fluid contacts the dry hydrogel material, the hydrogel matrix 1602 starts swelling within a very short time (seconds to minutes) and closes the delivery openings 1604 at the tip of the electrode 1600. As shown in FIG. 16C, the therapeutic fluid is now slowly released by the swollen hydrogel matrix 1603.

Although various exemplary embodiments of the invention have been disclosed, it should be apparent to those skilled in the art that various changes and modifications can be made which will achieve some of the advantages of the invention without departing from the true scope of the invention.

What is claimed is:

1. A cochlear implant electrode comprising:
   an implantable electrode carrier having an outer surface including a plurality of electrode contacts for electrically stimulating nerve tissue of the inner ear of a patient; and
   a drug lumen within the electrode carrier, the drug lumen having an inner surface and adapted to receive a therapeutic fluid and containing:
   i. one or more delivery openings disposed toward a distal end of the drug lumen and configured to permit the therapeutic fluid to flow to the outer surface of the electrode carrier, and
   ii. a coating of a dry hydrogel material disposed on at least a portion of the inner surface of the drug lumen, the coating covering the one or more delivery openings and adapted to swell in volume into a swollen hydrogel matrix that fills the drug lumen at its distal end when exposed to the therapeutic fluid
   wherein the hydrogel material is characterized by a pore size adapted to:
   i. release air from the drug lumen through the one or more delivery openings when the therapeutic fluid is added to the dry hydrogel material, and
   ii. control diffusion of the therapeutic fluid through the swollen hydrogel matrix within the drug lumen and through the one or more delivery openings to the outer surface of the electrode carrier.

2. An electrode according to claim 1, wherein the drug lumen is adapted to contain a treatment period amount of therapeutic fluid for an extended treatment period.

3. An electrode according to claim 1, wherein the hydrogel matrix has an adjustable pore size which controls diffusion rate of the therapeutic fluid.

4. An electrode according to claim 1, wherein the hydrogel matrix is based on hyaluronic acid.

5. An electrode according to claim 1, wherein the hydrogel matrix is based on a three-dimensional network of cross-linked hydrophilic polymer chains.

6. An electrode according to claim 1, wherein the hydrogel matrix has a mesh size small enough to resist entry of bacteria.

7. An electrode according to claim 1, wherein the therapeutic fluid includes dexamethasone.

8. An electrode array according to claim 1, wherein the electrode is adapted to release between 5 μg and 600 μg of dexamethasone during an initial 24 hour period of use.

9. An electrode according to claim 1, further comprising:
   a refilling arrangement for refilling the drug lumen in an implanted electrode with additional therapeutic fluid.

* * * * *